US011648148B2

(12) United States Patent
Kilbey

(10) Patent No.: US 11,648,148 B2
(45) Date of Patent: May 16, 2023

(54) HEAT TRANSFER VEST WITH HOOK AND LOOP SECUREMENT

(71) Applicant: Bryan E. Kilbey, DeFuniak Springs, FL (US)

(72) Inventor: Bryan E. Kilbey, DeFuniak Springs, FL (US)

( * ) Notice: Subject to any disclaimer, the term of this patent is extended or adjusted under 35 U.S.C. 154(b) by 86 days.

(21) Appl. No.: 15/645,206

(22) Filed: Jul. 10, 2017

(65) Prior Publication Data
US 2019/0008676 A1    Jan. 10, 2019

(51) Int. Cl.
*A61F 7/02* (2006.01)
*A41D 1/04* (2006.01)
*A41D 13/005* (2006.01)
*A61F 7/10* (2006.01)

(52) U.S. Cl.
CPC .............. *A61F 7/02* (2013.01); *A41D 1/04* (2013.01); *A41D 13/0051* (2013.01); *A41D 13/0056* (2013.01); *A41D 13/0058* (2013.01); *A61F 7/0241* (2013.01); *A41D 2300/32* (2013.01); *A41D 2300/322* (2013.01); *A61F 2007/0203* (2013.01); *A61F 2007/026* (2013.01); *A61F 2007/0215* (2013.01); *A61F 2007/0231* (2013.01); *A61F 2007/0233* (2013.01); *A61F 2007/0234* (2013.01); *A61F 2007/0244* (2013.01); *A61F 2007/0257* (2013.01); *A61F 2007/0292* (2013.01); *A61F 2007/108* (2013.01)

(58) Field of Classification Search
CPC ........ A61F 2007/0234; A61F 2007/023; A61F 2007/0268; A61F 2007/0244; A61F 7/02; A61F 7/0241; A61F 2007/0203; A61F 2007/0215; A61F 2007/0231; A61F 2007/0233; A61F 2007/0257; A61F 2007/026; A61F 2007/0292; A61F 2007/108; A41D 1/04; A41D 13/0056; A41D 13/01; A41D 13/0051; A41D 13/0058; A41D 2300/32; A41D 2300/322
See application file for complete search history.

(56) References Cited

U.S. PATENT DOCUMENTS

| | | | |
|---|---|---|---|
| 5,800,491 A | | 9/1998 | Kolen et al. |
| 6,125,645 A | * | 10/2000 | Horn .................. A41D 13/0056 2/458 |
| 8,105,371 B1 | * | 1/2012 | Giocondo, Jr. .......... A41D 1/04 607/108 |
| 9,039,747 B2 | | 5/2015 | Nebolon et al. |
| 2002/0069448 A1 | * | 6/2002 | Appolonia ......... A41D 13/0056 2/102 |
| 2002/0152533 A1 | * | 10/2002 | Lesley ................... A41D 13/01 2/102 |
| 2004/0147991 A1 | * | 7/2004 | Lu ............................. A61F 7/03 607/114 |
| 2006/0036304 A1 | * | 2/2006 | Cordani .................... A61F 7/03 607/108 |

(Continued)

*Primary Examiner* — Adam Z Minchella
(74) *Attorney, Agent, or Firm* — J. Wiley Horton

(57) ABSTRACT

The present invention comprises a heat transfer vest. The vest is configured to mount a plurality of heat transfer packs on its interior surface. In the preferred embodiments the appropriate portions of the interior surface are covered in a hook-compatible material. In these versions, the thermal transfer packs include one or more hook panels that are used to attach the packs to the interior surface.

15 Claims, 13 Drawing Sheets

(56) References Cited

U.S. PATENT DOCUMENTS

| | | | |
|---|---|---|---|
| 2008/0040831 A1* | 2/2008 | Nilforushan | A61F 7/02 219/211 |
| 2010/0287681 A1* | 11/2010 | Storms, Jr. | F41H 1/02 2/102 |
| 2012/0232621 A1* | 9/2012 | Kriksunov | A61F 7/034 607/114 |
| 2013/0126511 A1* | 5/2013 | Yulee | A41D 1/04 219/211 |
| 2014/0316493 A1* | 10/2014 | Kilbey | A61F 7/10 607/108 |
| 2015/0150313 A1* | 6/2015 | Huckins | A41D 13/0053 62/259.3 |
| 2016/0249691 A1* | 9/2016 | Gordon | A41D 1/04 2/102 |
| 2018/0161615 A1* | 6/2018 | Feng | A63B 21/065 |

\* cited by examiner

HEAT TRANSFER VEST WITH HOOK AND LOOP SECUREMENT

BACKGROUND OF THE INVENTION

1. Field of the Invention

This invention relates to the field of garments. More specifically, the invention comprises a wearable vest that transfers heat to a wearer or absorbs heat from a wearer.

2. Description of the Related Art

Outer garments have long been used to regulate heat transfer from a human wearer. Most garments serve to reduce heat loss on cold days, and vests have been used for this purpose for many years. In more recent times some garments have been used to absorb heat from the wearer. In the field of sports medicine, it is now well understood that pre-cooling an athlete enhances performance during an event. In addition, cooling an athlete immediately after an event often aids in recovery.

In the pre-cooling scenario, the body's core temperature must be reduced. As the human body seeks at all times to maintain a fixed core temperature, a substantial heat transfer is required to create the desired reduction. An outer garment may be used to locate a suitable heat transfer medium against the user's torso. The temperature of the transfer medium must be significantly below the user's skin temperature. However, a temperature difference that is too great will cause tissue damage. The use of a garment-based heat transfer mechanism therefore presents the competing concerns of (1) a temperature difference that is great enough to transfer sufficient heat, and (2) a temperature difference that is small enough to a void tissue damage.

A heat transfer medium that undergoes a phase change offers advantages. First, the use of a phase change allows the absorption of much more heat that would be possible in its absence. Second, the use of a phase change provides a steady temperature for the heat transfer medium as it is transitioning from a solid to a liquid (the temperature of a substance being constant in that process).

One suitable heat transfer medium is disclosed in U.S. Pat. No. 5,800,491 to Kolen and Nebolon. This patent discloses a hydrating liquid consisting of a solution of water and a humectant selected from the group consisting of propylene glycol, ethylene glycol, glycerin, dimethyl sulfoxide, dimethyl formamide, and combinations thereof. Upon freezing, these solutions create a solid state that is akin to packed snow or crushed ice. It remains pliable instead of freezing into a unified solid mass. More recent developments regarding this type of heat transfer medium are disclosed in U.S. Pat. No. 9,039,747 to Nebolon and Gardner.

It is known in the art to provide heat transfer packs such as disclosed in the '491 and '747 Patents. These packs are typically placed in a pocket formed as part of a securing wrap or garment. These have been used in medical applications for cooling therapy (such as following knee surgery). Recently such packs have been used for pre-cooling in the field of sports medicine, post cooling to aid in recovery, and precooling for high heat environments.

Beyond the field of athletics, research data now indicates that human performance is adversely affected by heat in many different environments. For example, industrial production facilities often have elevated ambient temperatures. Some facilities operate with ambient temperatures between 32 and 40 degrees centigrade (90 and 104 degrees Fahrenheit). A metal forging factory experiences this range of temperatures, particularly in the summer.

The human body can tolerate these temperature indefinitely, but it is now understood that performance will be adversely affected. This degradation leads to lower productivity, cognitive performance loss, and even an increase in workplace accidents. In fact, European regulatory agencies are not considering restricting the length of exposure to such temperatures.

A heat transfer garment can enhance the productivity of workers in these high-heat environments. A suitable garment can allow a human operator's core temperature to remain normal even when the operator is surrounded by a hot environment.

Of course, the effects of cold temperatures on human performance may be just as pronounced. In cold environments it may be desirable to provide a garment that actually transfers heat to the wearer (as opposed to simply reducing the heat loss rate from the wearer).

The present invention provides a heat transfer garment that may be used to enhance human performance in many applications.

BRIEF SUMMARY OF THE PRESENT INVENTION

The present invention comprises a heat transfer vest. The vest is configured to mount a plurality of heat transfer packs emits interior surface. In the preferred embodiments the appropriate portions of the interior surface are covered in a hook-compatible material (such as VELCRO loop material). In these versions, the thermal transfer packs include one or more hook panels that are used to attach the packs to the interior surface.

For the versions intended to absorb heat from the wearer, the thermal transfer packs preferably contain a heat transfer medium that undergoes a phase change from a solid to a liquid well below human body temperature. The medium preferably also transitions to a "soft" solid skin to packed snow or crushed ice. The packs also include a cover material on the side facing the user. This cover material provides some insulation between the wearer and the cold heat transfer medium. It preferably also provides a wicking action to that moisture is not trapped.

While primarily intended for cooling applications the inventive vest may also be used for heating applications. In these embodiments, the temperature of the thermal transfer packs is initially above that of human body temperature.

Figure 1:
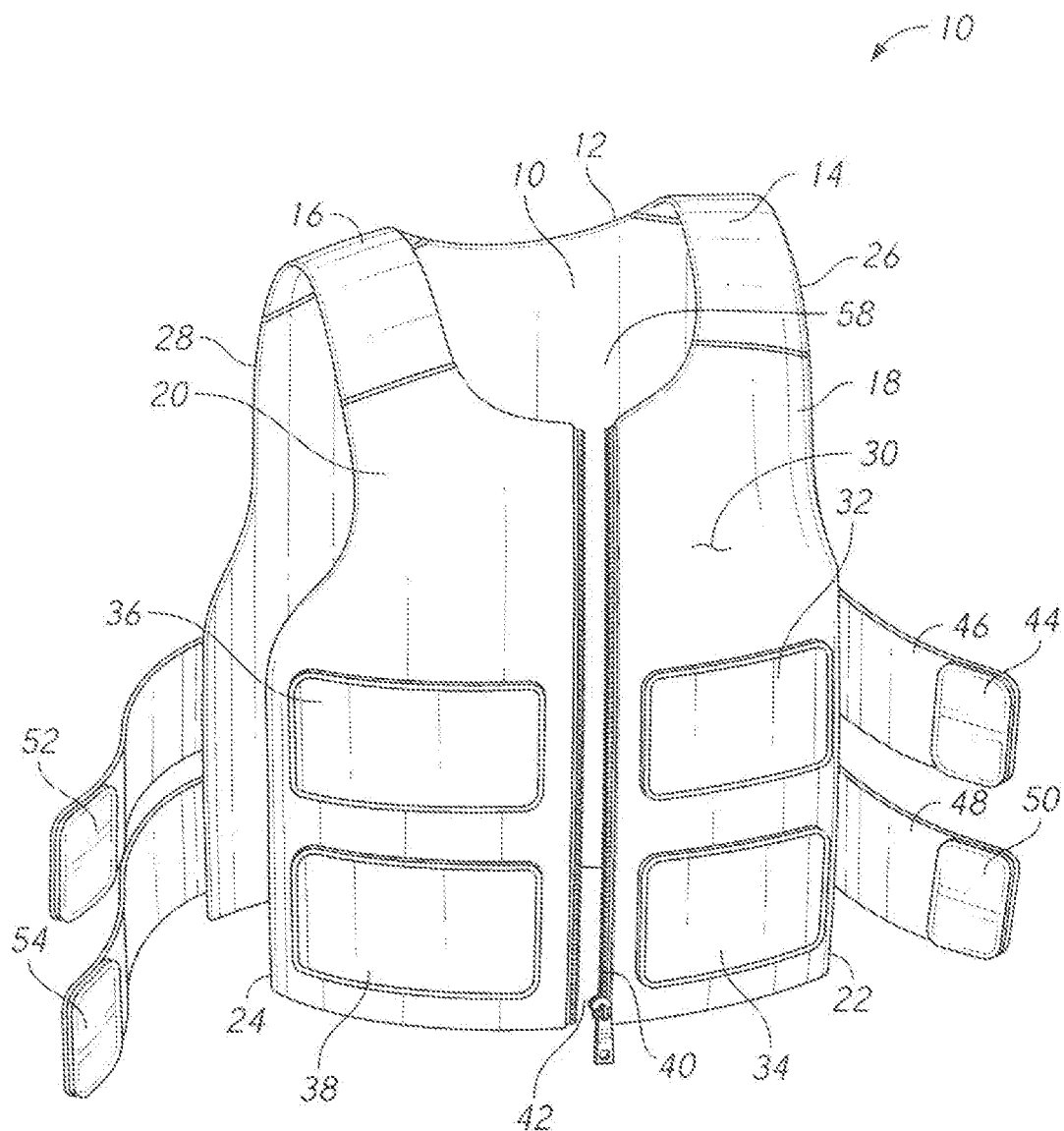
FIG. 1 is a perspective view, showing the inventive vest.

REFERENCE NUMERALS IN THE DRAWINGS 10 heat transfer vest
12 neck relief
14 left yoke panel
16 right yoke panel
18 left front panel
20 right front, panel
22 left front lateral extension
24 right front lateral extension
26 left arm relief
28 right arm relief
30 exterior surface
32 left upper loop panel
34 left lower loop panel
36 right upper loop panel
38 right lower loop panel
40 zipper
42 vertical break
44 hook panel
46 upper strap
48 lower strap
50 hook panel
52 hook panel
54 hook panel
56 slider body
58 interior surface
59 user
60 overlap
62 thermal transfer pack
64 valve
66 hook panel
68 sealed perimeter
70 interior
72 heat transfer medium
74 sealing material
76 cover material
78 left upper side pack
80 side pack
82 upper back pack
84 back pack
86 outline
88 label
90 exterior layer
92 insulating layer
94 reflective layer
96 loop material
98 shawl collar
100 elevated posterior edge
102 cranial pack
104 neck covering collar
106 loop tab
108 book panel
110 sub jaw edge
112 opening
114 snap closure
116 carotid bag
118 waterproof layer
120 evaporative layer
122 sub-bag
124 composite thermal transfer bag
126 lower edge

DETAILED DESCRIPTION OF THE INVENTION

FIG. 1 shows a perspective view of a preferred embodiment of the present invention. Heat transfer vest 10 may be used to absorb heat from a wearer/user or transfer heat to a wearer/user. Those skilled in the art will know that a vest may be constructed in a variety of ways. The version shown in FIG. 1 should not be viewed as limiting the invention to any particular example.

Back panel 10 is configured to rest against the user's back. Left front panel 18 and right front panel 20 are configured to rest against the anterior portion of the user's abdomen and chest. Left and right yoke panels 14, 16 pass over the users shoulders and joint the left and right front panels 18, 20 to back panel 10. Seams are shown where these various panels are joined, but seams will not always be present. In some versions the vest may be made of one contiguous panel or some other configuration of multiple panels.

The two front panels meet at vertical break 42, which is selectively closed using zipper 40. Right front panel 20 includes right front lateral extension 24. Left front panel 18 includes left front lateral extension 22. The two lateral sides of back panel 10 preferably include lateral extensions as well. Left arm relief 26 and right arm relief 28 lie above the region of the lateral extensions.

The lateral extensions are configured to overlap in order to adjust the overall circumference of the vest when it is donned by a user. The vest preferably includes adjustable securement mechanisms so that it can fit a wide variety of users. In the version shown in FIG. 1, the securement mechanisms include two straps—upper strap 46 and lower strap 48. The two straps are secured to the outward facing surface of back panel 10. The straps in this example include elastic material so that they can be stretched, and allow for compression of the thermal packs against the user's body.

The free end of each strap includes a hook panel. These are hook panels 44, 50, 52, and 54. Loop panels 32, 34, 36, and 38 are provided on exterior surface 30 of left front panel 18 and right front panel 20. The vest is designed so that it can be adjusted by the user. One good approach to adjusting the vest is to first don the vest and then zip up zipper 40 to close vertical break 42. The user then pulls the two straps tight and presses the hook panels on the free ends of the straps against the loop panels on the outward facing surface of the vest. For example, the user might first secure hook panel 52 to right upper loop panel 36. The user would then draw the upper strap to a desired level of tightness before securing hook panel 44 to left upper loop panel 32.

Next, the user secures hook panel 54 to right lower loop panel 38. Then he or she secures hook panel 50 to left lower loop panel 34. The position of the hook panels can be iteratively adjusted to achieve a comfortable fit. Compression of the transfer packs against the body is desirable to obtain a suitable rate of heat transfer. The two lateral gaps in the vest allow a very wide range of adjustment. An elastic functionality for straps 46, 48 is desired since this allows the user to stretch the straps and secure them—thereby providing a desired level of inward compression.

Ordinarily the straps will be disconnected each time the user removes the vest. Alternatively, once a comfortable fit is achieved, the hook panels may be left in place. The user then removes the vest by unzipping zipper 40 and secures it hack in place (when desired) by using the zipper again.

Figure 2:
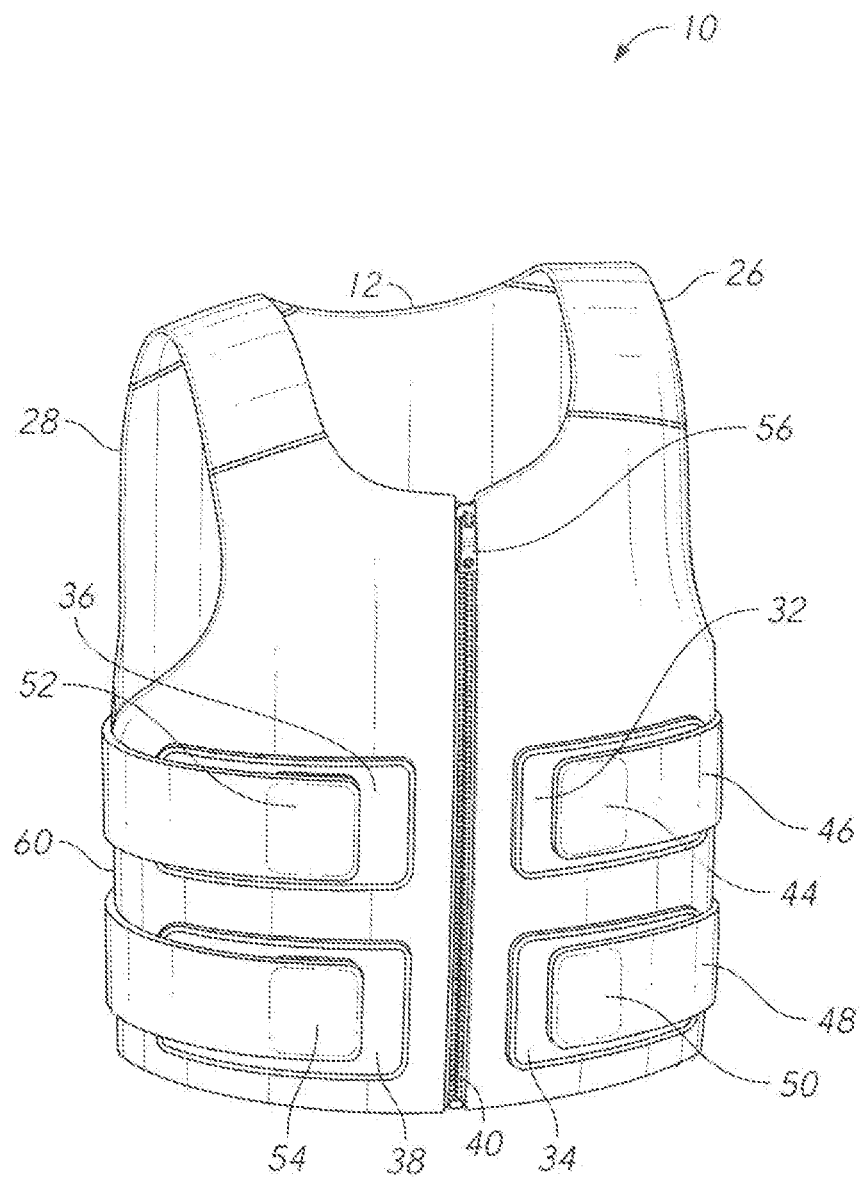
FIG. 2 is a perspective view, showing the inventive vest in a closed configuration as it would be worn by a user.

FIG. 2 shows heat transfer vest 10 after the adjustable securement mechanisms have been secured. The reader will observe that the lateral extensions have been overlapped to create overlap 60. For many individuals the overlap may not exist and in fact the lateral extensions on the front panels may not even reach the lateral extensions on the back panel. Neck relief 12 is provided for the user's neck. Left and right arm reliefs 26, 28 are provided for the user's arms. The reader will note that slider body 56 has been moved upward to its full extent in order to close zipper 40 and lock the two front panels together.

Figure 3:
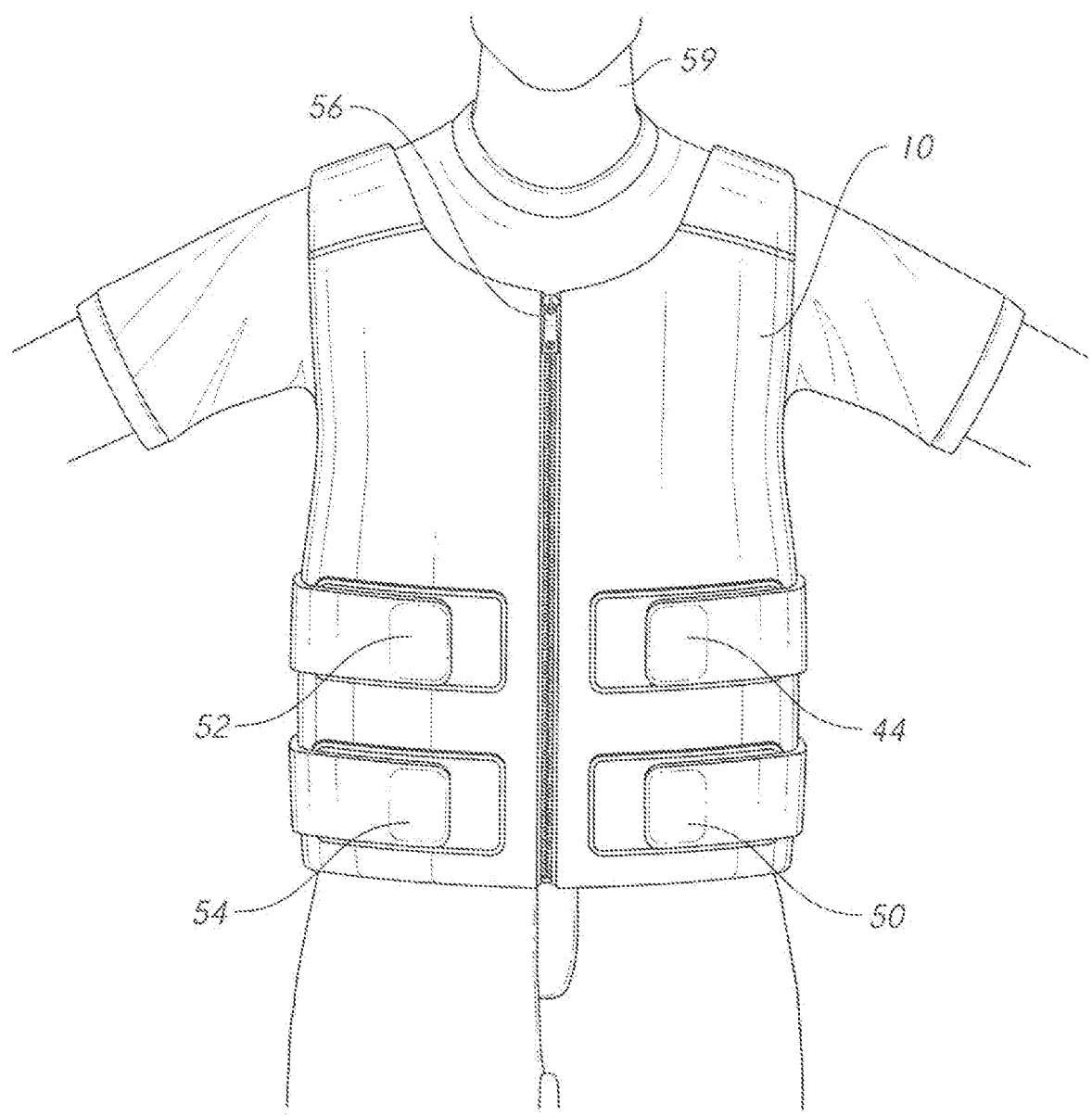
FIG. 3 is a perspective view, showing the inventive vest being worn by a user.

FIG. 3 shows the inventive vest being worn by user 59. The reader will observe how the neck and arm reliefs accommodate the user's anatomy. The straps in this version completely encircle the back of the vest. It is of course also possible to use four straps instead of two. Each hook panel would be mounted on its own individual strap. The end of each strap opposite its hook panel would be attached to the exterior of back panel 10.

The neck and arm reliefs may be different for different applications. One application for the vest is a hot industrial environment. In this sort of environment a worker may need considerable freedom of movement. In such a case, the neck and arm reliefs may be enlarged to accommodate anticipated head and arm movements.

Figure 4:
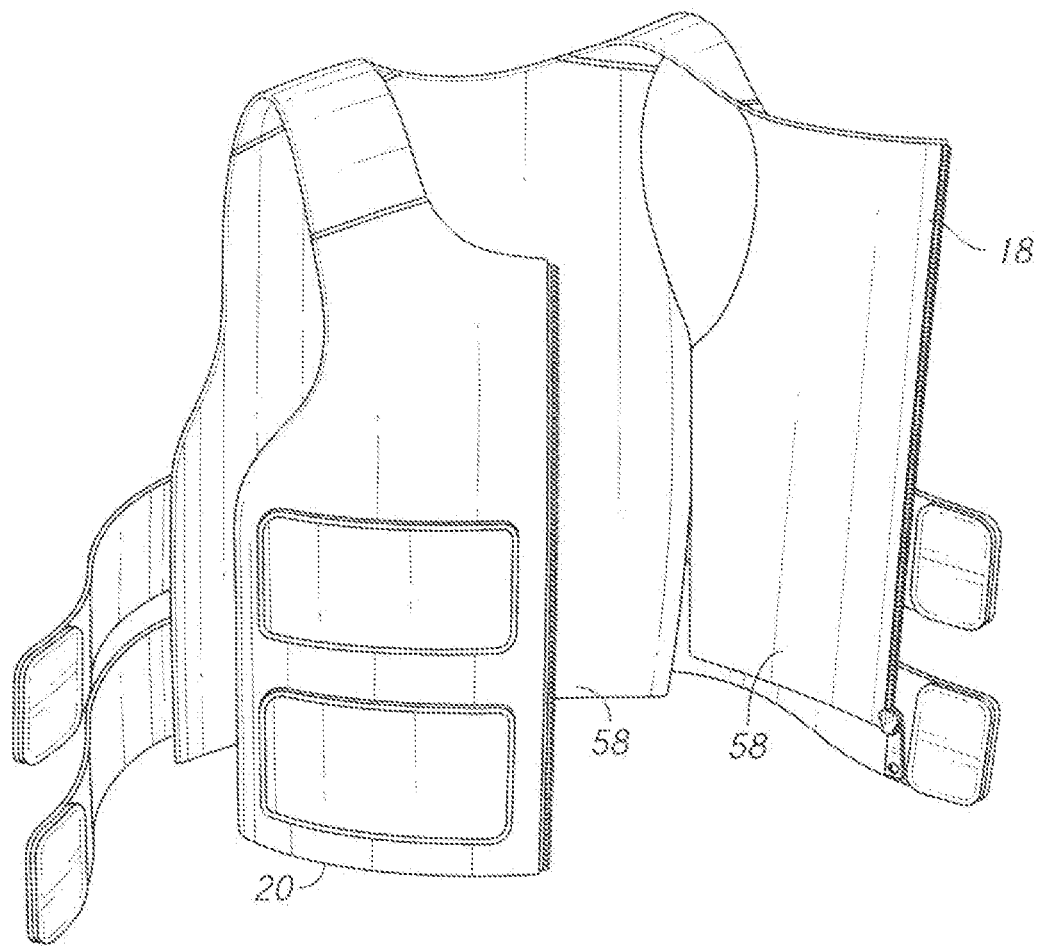
FIG. 4 is a perspective view, showing the inventive vest with the left side rotated open so that both the interior and exterior surfaces can be viewed.

The inventive vest uses thermal transfer packs that are directly attached to its interior surfaces (as opposed to being placed in a pocket). FIG. 4 shows the same embodiment as depicted in FIGS. 1-3. However, in FIG. 4, the zipper has been unzipped and left front panel 18 has been urged open as shown. Interior surfaces 58 of the front panels and back panel are covered in loop material that is suitable for engagement by hook panels on the thermal transfer packs. It is not necessary to cover all of the interior surfaces, but the majority of these surfaces preferably are covered so that the thermal transfer packs can be placed in a variety of locations. As an example, the loop covering may be selectively omitted from the areas up near the yoke panels if the user does not desire to place a thermal transfer pack in those locations.

Figure 5:
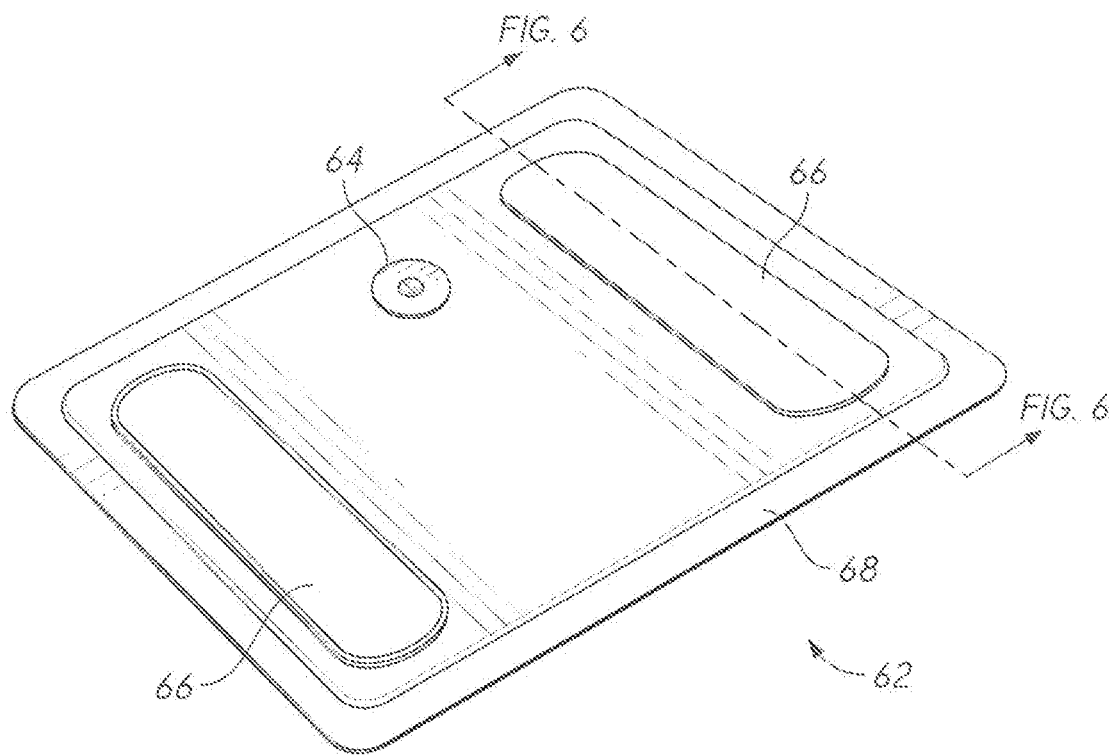
FIG. 5 is a perspective view, showing a thermal transfer pack as used in the present invention.
Figure 6:
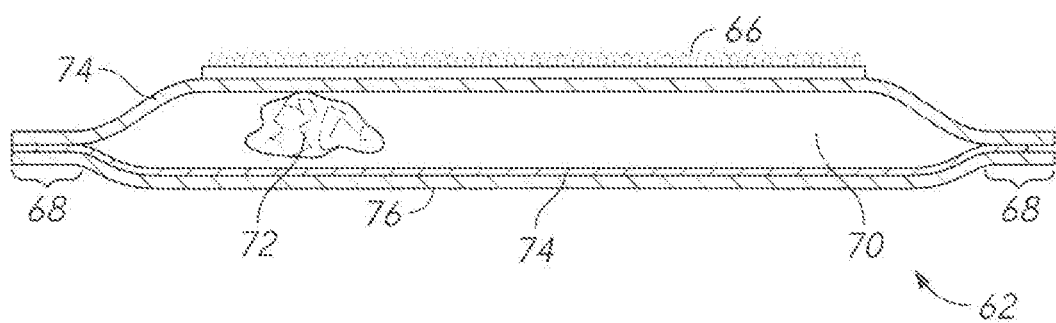
FIG. 6 is a sectional elevation view, showing the construction of the thermal transfer pack of FIG. 5.

FIGS. 5 and 6 illustrate exemplary embodiments for the thermal transfer packs used in the present invention. In FIG. 5, thermal transfer pack 62 includes two liquid-impermeable layers joined together along a sealed perimeter 68 to create an enclosed volume. Valve 64 provides a controlled passage from the exterior to the interior. The interior contains a heat transfer medium. This is preferably a hydrating liquid consisting of a solution of water and a humectant selected from the group consisting of propylene glycol, ethylene glycol, glycerin, dimethyl sulfoxide, dimethyl formamide, and combinations thereof (as described in the prior art section of this disclosure).

When this substance transitions to a solid it expands to a form that is similar to packed snow or crushed ice. Air is admitted to the Interior through valve 64 during the freezing process. When the medium melts valve 64 allows air out of the enclosed interior but not the liquid medium. Hook panels 66 are provided to attach thermal transfer pack 68 to the interior surface of the inventive vest (via the loop covering thereon).

FIG. 6 shows a section view through thermal transfer pack 62. Two layers of sealing material 74 (the water impermeable layer) are staked together to form sealed perimeter 68. Each pack has an inward feeing surface and an outward facing surface. The inward facing surface includes a layer of cover material 76. The cover material is preferably a soft and compliant material that may be comfortably worn against the user's thin clothing (such as a T-shirt) or even directly against the user's skin. This material preferably wicks moisture away from the user as well.

Cover material 76 may be bonded to the thermal transfer pack by any suitable method—including adhesives or stitching. It is preferable for the side facing the user to have no exposed discontinuities as these may be irritating.

Heat transfer medium 72 is contained within interior 70 formed between the two layers of sealing material 74. Hook panel 66 is affixed to the outward-facing side of the assembly. The soft and pliable cover material 76 faces toward the user. Hook panel 66 faces away from the user and toward the loop covering on the inside of the vest.

Figure 7:
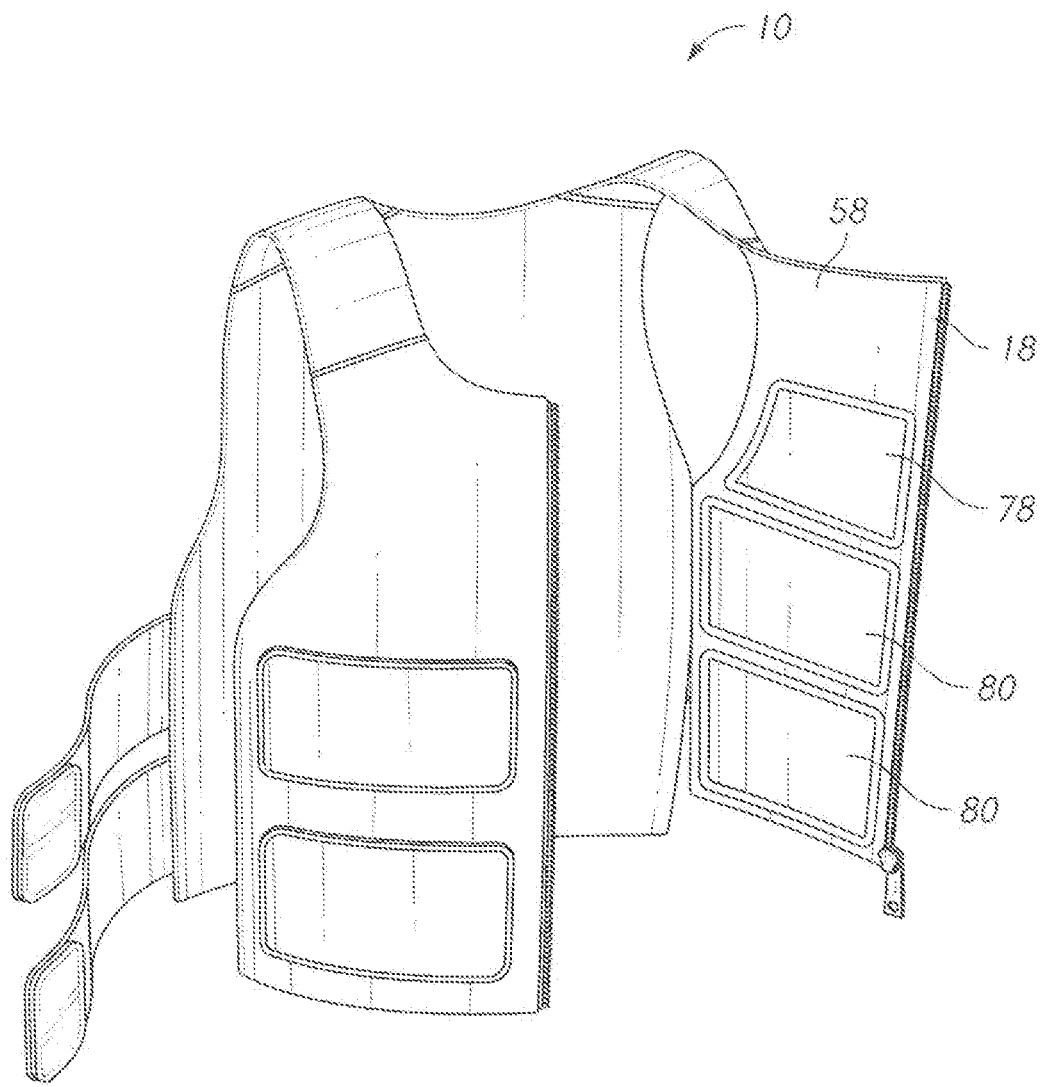
FIG. 7 is a perspective view, showing the application of thermal transfer packs to the inside of the left front panel.

FIG. 7 shows the inventive heat transfer vest 10 open as shown previously in FIG. 5. Three thermal transfer packs have been affixed to interior surface 58 of left front panel 18. The thermal transfer packs may be shaped to conform to the available surface area on the vest's interior. In the example of FIG. 7, left upper side pack 78 (a particular shape for a thermal transfer pack) includes a cutaway conforming to the perimeter of left arm relief 26. The two side packs 80 are larger. They are simple rectangles as this shape conforms to the space available in the lower portion of left front panel 18.

Figure 8:
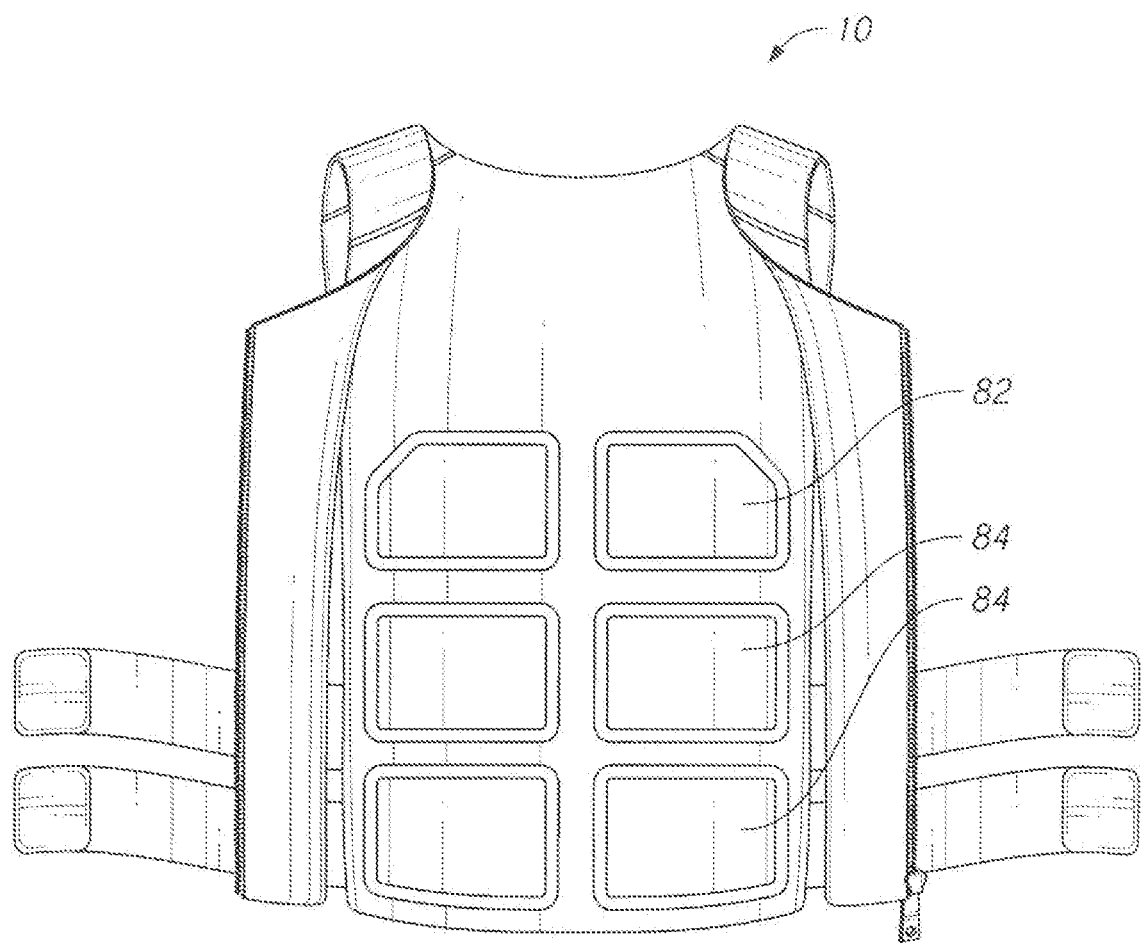
FIG. 8 is a perspective view, showing the application of thermal packs to the inside of the back panel.

FIG. 8 shows a front perspective view of the vest with both side panels folded away to show the interior surface of the back panel. Two upper back packs 82 (another shape for the thermal transfer pack) are affixed as shown. These packs include a cutaway near the upper outside corner to facilitate shoulder mobility. Four rectangular hack packs 84 are also affixed as shown.

The use of the hook-and-loop connection between the thermal transfer packs and the vest means that the user may move the packs to many desired locations and may "customize" the configuration to suit his or her preferences. In some instances, however, it may be desirable to provide a "standard" placement for some of the packs.

Figure 9:
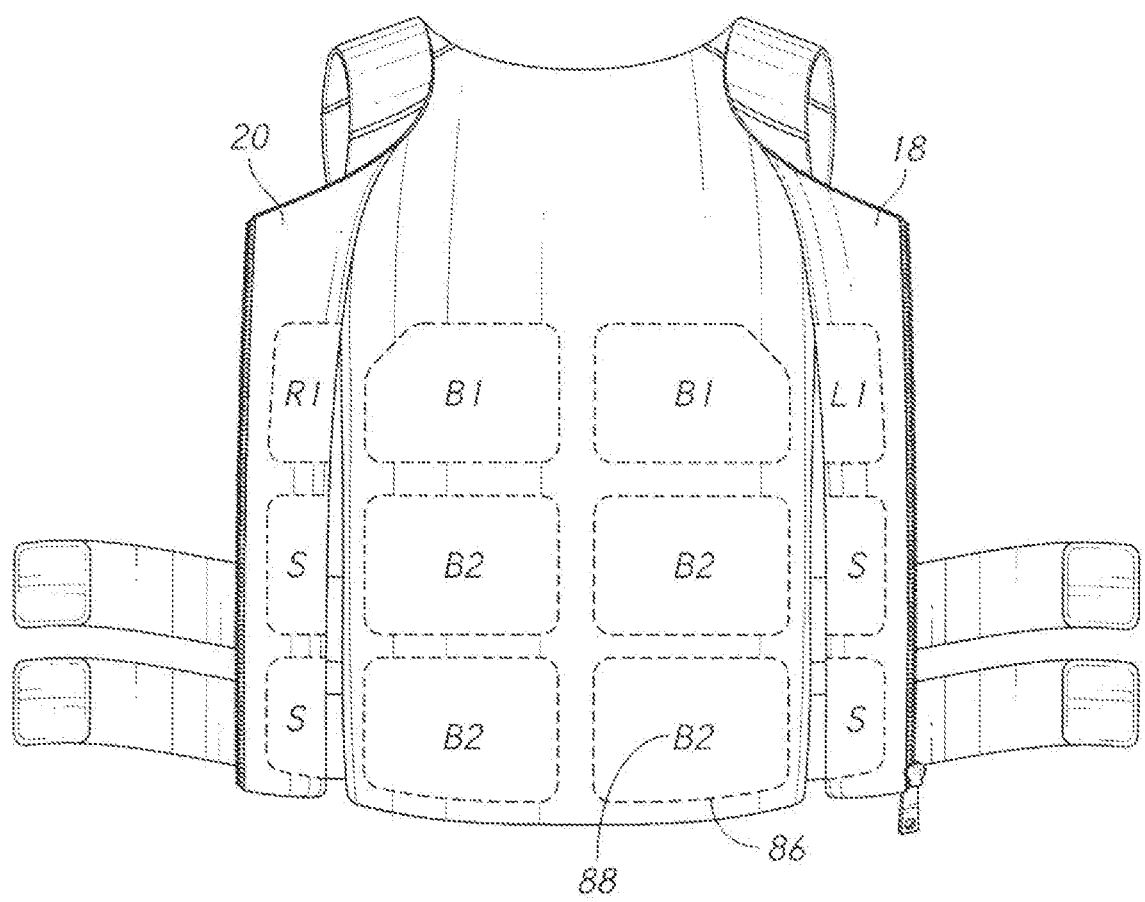
FIG. 9 is a perspective view, showing the use of outlines and labels on the interior surfaces of the vest to aid in fixe placement of the thermal transfer packs.

Standard locations may be marked on the vest's interior, FIG. 9 shows one way in which this may be done. Outlines 86 are screen printed as dashed lines on the interior. Other indicators of position may be used (such as indicating the location of the corners of each pack). Labels 88 may also be provided to indicate a particular type of thermal transfer pack that should be used in this location. The user may employ these outlines and labels to place some or all of the packs shown.

Once the desired thermal transfer packs are in position, the user may don the vest and adjust it for a suitable fit as shown in FIGS. 2 and 3. Some user may like a loose fit and some will want a tighter fit (a tighter fit is preferable from a heat transfer standpoint). Once the straps are adjusted, the fit can be maintained. The user employs the zipper to remove and replace the vest.

The use of the hook-and-loop fasteners makes replacement of the thermal packs easy and convenient. If the user is working in a hot environment (and therefore using thermal transfer packs intended to cool), the packs will need to be changed approximately every four hours. A fresh supply of replacement packs can be prepared in a freezer. The user takes off the vest and lays it out as shown in FIG. 9. The user removes the packs on the vest and replaces them with new, frozen packs. The removed packs can then be placed in the freezer so that they will be ready at the next interval.

Figure 10:
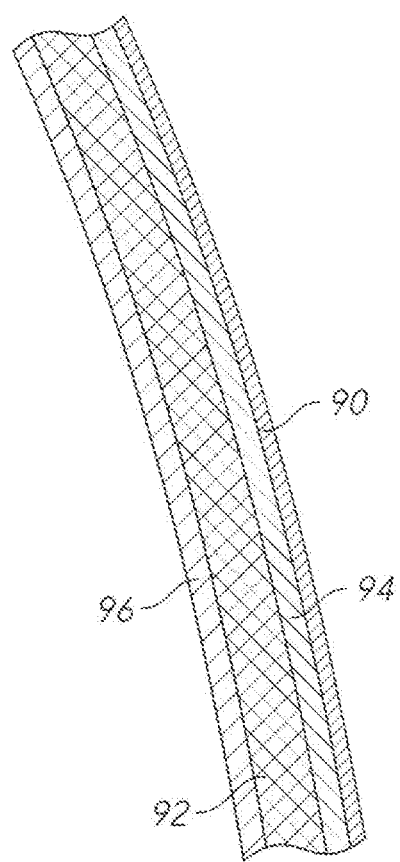
FIG. 10 is a sectional elevation view, showing a representative layering of materials for the inventive vest.

The inventive vest may incorporate other features to enhance its performance. FIG. 10 shows a section view through the vest. Multiple layers are employed in this example. Exterior layer 90 is preferably a tough fabric. It may also be water and fire resistant Reflective layer 94 is provided adjacent to exterior layer 90 to reduce the heat transfer from the ambient environment to the thermal transfer packs. It preferably serves as a UV barrier. It may be a distinctive material—such as a thin metal foil. On the other hand, it may be a coating that is applied over one of the other layers. Insulating layer 92 provides cushioning and insulation. It may be made of foam or it may be made of quilted layers containing fiber-fill or other similar materials. Loop material 96 comprises the innermost layer.

Throughout this disclosure, the term "loop material" should be understood to mean any material that is compatible with a hook panel so that the hook panel will adhere to the loop material. The term encompasses traditional VELCRO loop material but it encompasses many other materials as well.

Figure 11:
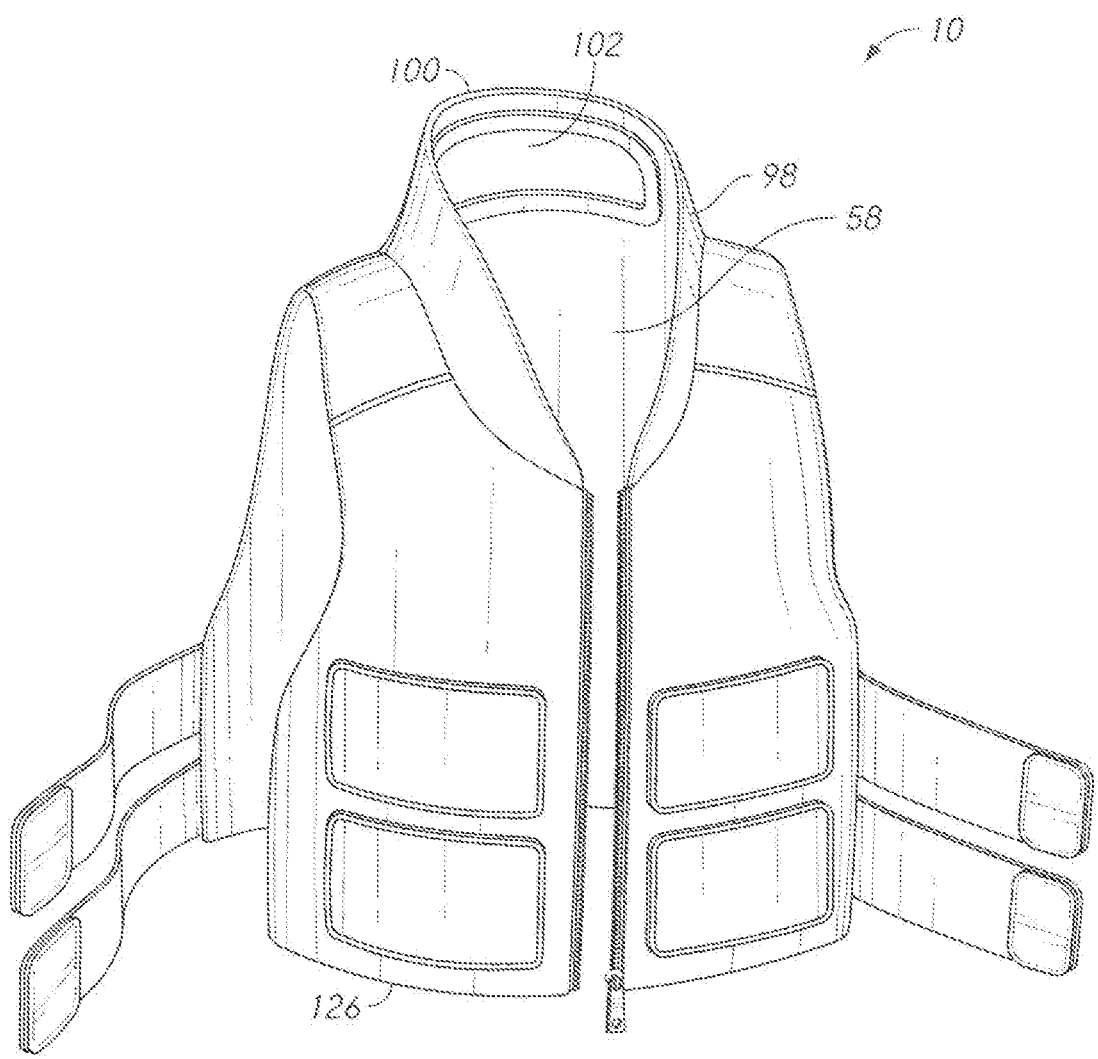
FIG. 11 is a perspective view, showing an alternate embodiment of the inventive vest with an elevated posterior neck portion.

FIG. 11 shows an alternate embodiment of heat transfer vest 10 that is well suited to the treatment of multiple sclerosis ("MS") patients. MS patients benefit from the addition of cold therapy during exercise. However, MS patients often also suffer from digestive issues and the application of cold therapy to the abdomen is generally undesirable. In the embodiment of FIG. 11, the overall height of the vest is reduced so that lower edge 126 rests along the lower extreme of the wearer's rib cage.

MS patients may also benefit from additional cooling applied to the back of the neck and the lower posterior portions of the skull (other users may obviously benefit from cooling applied to these areas as well). Shawl collar 98 is provided in the version of FIG. 11. The shawl collar includes elevated posterior edge 100. Cranial cold pack 102 may be applied to interior surface 58 (as explained previously) just below elevated posterior edge 100.

The shawl collar preferably includes elastic functionality so that the cranial pack will be urged against the user's neck and head. The entire shawl collar may be made of elastic material (such as an elastic neoprene) or elastic panels may be provided in inelastic material.

Figure 12:
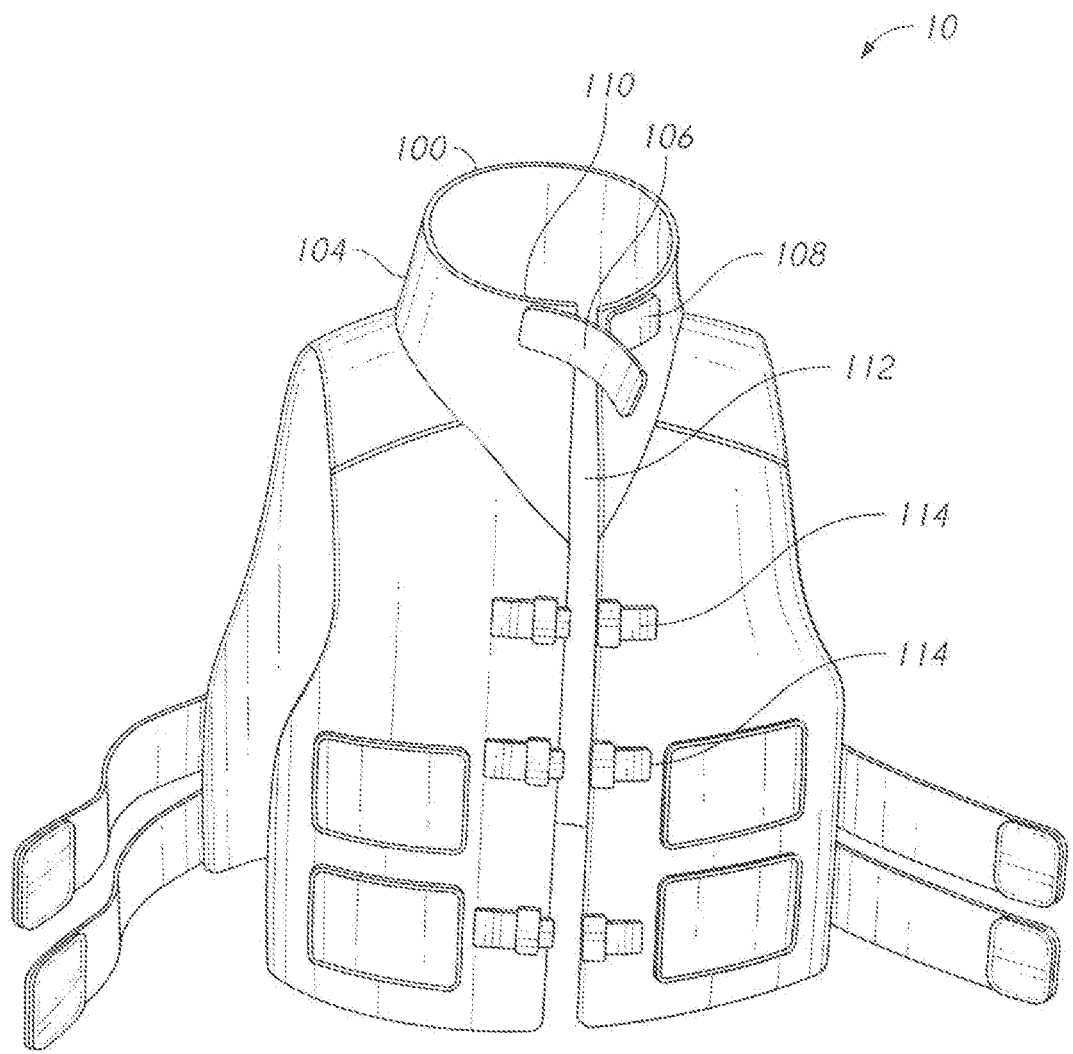
FIG. 12 is a perspective view, showing an alternate embodiment of the inventive vest with an elevated posterior and anterior neck portion.

FIG. 12 shows a third embodiment of the inventive vest. It has been demonstrated that heat transfer packs applied to the front of the neck can be quite effective, as these press against the carotid arteries supplying blood to the brain. The version shown in FIG. 12 features neck-covering collar 104. This collar includes a raised anterior sub-jaw edge 110 in addition to elevated posterior edge 100. The anterior portion includes an opening 112. The user may close this opening by pressing loop tab 106 against hook panel 108.

Figure 13:
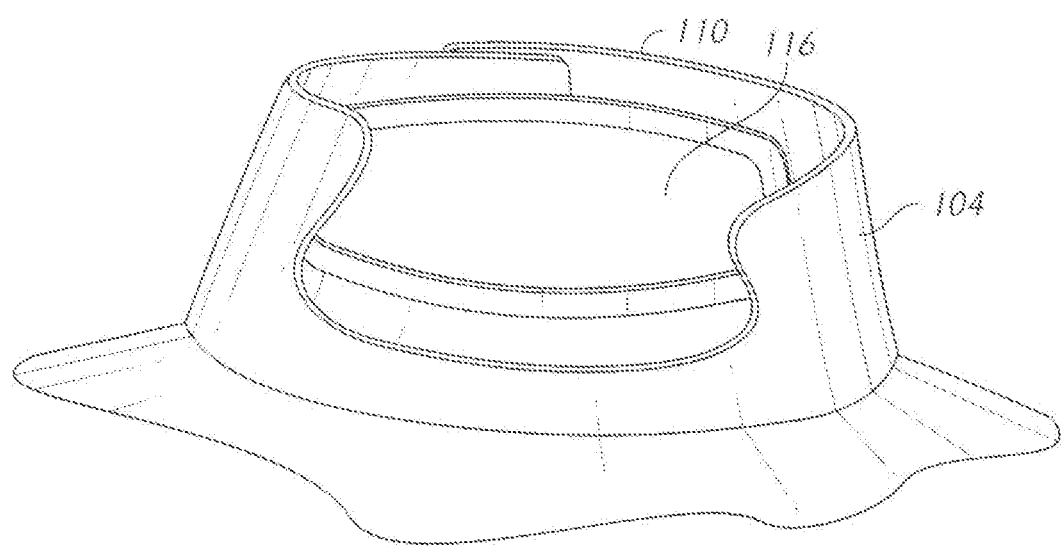
FIG. 13 is a rear perspective view with a cutaway, showing the placement of a carotid bag.

FIG. 13 shows a view of the same embodiment from the rear. The rear portion of neck-covering collar 104 has been cutaway to reveal the interior of the collar. Carotid bag 116 is attached to the interior surface of the anterior neck portion by pressing a hook panel or panels on the carotid bag against a loop covering on the interior of the collar. The carotid bag may be applied with the collar still open. The user presses the bag against the left (interior) portion of the collar. The user then closes the right portion of the collar over the bag and presses the loop panel into place to secure it.

Returning again to FIG. 12, the reader will note that the closure device provided for the front of the vest in this embodiment if three snap closures 114 rather than a zipper. Any suitable closure mechanism can be used, including hook-and-loop panels, buttons, or buckles.

Figure 14:
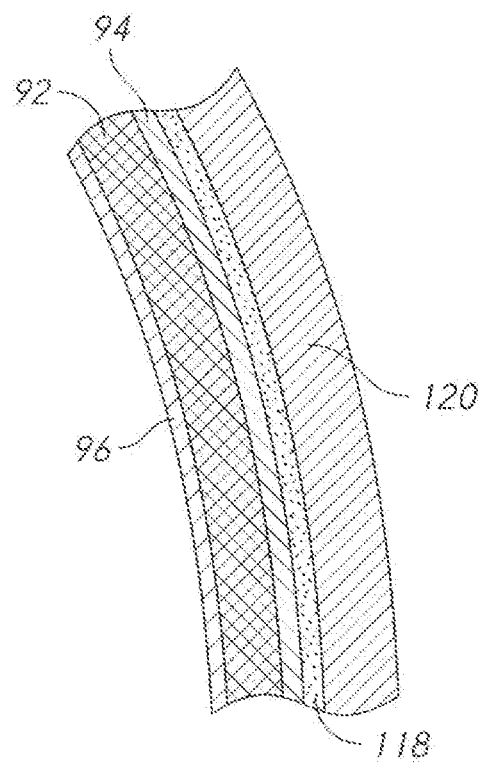
FIG. 14 is a sectional elevation view, showing an alternate representation of the layering of materials for the inventive vest.

FIG. 14 shows a section view through another alternate embodiment of the vest. Loop material 96, insulating layer 92, and reflective layer 94, and insulating later 96 are arranged as shown in the version of FIG. 10. However, waterproof layer 118 may be provided over insulating layer 96 (on the outside of the insulating layer). Evaporative layer 120 lies over the top of waterproof layer 118. The evaporative layer comprises a porous substance that can be wetted to retain water. The retained water then evaporates as external heat is applied to the vest. This provides an interval of evaporative cooling.

Waterproof layer 118 prevents the water in evaporative layer 120 seeping inward. Of course, as those skilled in the art will know, waterproof layer 118 may include materials that allow wafer to pass outward through the layer but prevent water passing inward. In use, the outside of the jacket can be wetted (such as by pouring or spraying). The outside may also be rewetted at intervals to prolong the evaporative cooling effect.

Any of the known evaporative cooling fabrics could be used for evaporative layer 120. In some embodiments, the vest could simply be constructed as an evaporative cooling layer 120 on the outside of a layer of loop material 96. The vest in this instance would have cold packs affixed to the loop material and an evaporative cooling layer over the top. A single material could also be used for the evaporative cooling layer and the layer of loop material (which could then he made as a single layer).

Figure 15:
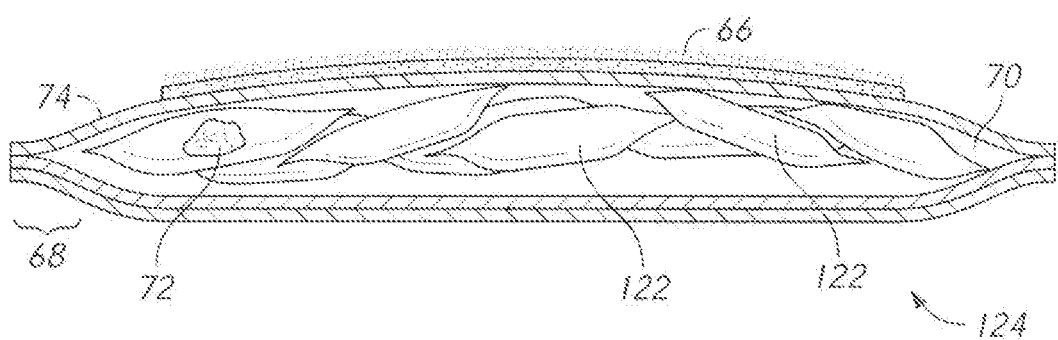
FIG. 15 is a sectional elevation view, showing the construction of an alternate thermal transfer pack using a plurality of sub-bags.

FIG. 15 shows an enhancement to the cooling pack described in FIG. 6. Rather than placing the cooling media in a single compartment, the version of FIG. 15 places several small bags of cooling media into a larger bag. Sub-bags 122 are relatively small—on the order of 1 to 2 inches square. As explained previously, the cooling media contained within interior 70 is preferably a substance such as shown in U.S. Pat. No. 5,800,491 to Kolen and Nebolon. This substance forms an organized crystalline solid with a consistency similar to snow. Even as a solid, it remains soft and malleable. However, the substance such as disclosed in the '491 Patent does not absorb as much energy during the transition from a solid to a liquid as pure water. Water can absorb more thermal energy, yet water has an undesirable property in that it solidifies into a hard mass (ice). If bag 124 were simply filled with water and frozen, the result would be a rigid object that would be quite uncomfortable to wear.

The construction of FIG. 15 provides the advantageous latent heat of water while retaining most of the beneficial aspects of the substance described in the '491 Patent. Each sub-bag 122 is filled with water. Small amounts of other substances may be present as well, hut water is by far the main constituent. The volume contained within interior 70 but outside sub-bags 122 is filled with a substance that creates a snow-like solid (such as described in the '491 Patent). The result is an advantageous combination of features. Each individual sub-bag 122 freezes into a hard object (containing ice). The surrounding volume freezes into a malleable snow-like substance. The sub-bags are relatively small—preferably less than 3 cm on a side. Thus, the overall thermal transfer bag 124 can still bend and flex because the sub-bags 122 move about within the snow-like frozen substance surrounding them. The user employs the composite bag 124 in the same way. However, the composite nature of the bag allows a greater absorption of thermal energy for the same unit volume.

In some versions of the composite thermal transfer bag the sub-bags or outer bag can be include a thermochromatic material. This material changes color when the media freezes—thereby clearly indicating to the user whether all the sub-bags are fully transitioned to a solid. In some versions a thermochromatic ink may be added to the water within sub-bags 122. In other versions, the thermochromatic material will be a film added to the sub-bags, the overall bag, or both.

The various embodiments of the invention may include one or more of the following features:

1. The back panel yoke panels, and front panels may be made as one integral piece.

2. The back panel and front panels combine to encircle the user around the torso. Breaks in this circumference may be provided at various places (as well as potential overlaps) to allow the circumference of the encirclement to be adjusted so that the vest may fit different size users.

3. The loop covering may cover the entire interior surface of the vest. On the other hand, it may only include a band passing around the region of the user's navel.

4. The vest may be used with hot packs configured to transfer heat to the user. These hot packs may also incorporate a phase change.

5. The vest may be used with cold packs based on gel technology.

6. The closure mechanisms may include buckles or snaps rather than hook-and-loop devices.

7. The vest may be made in different sizes. For some versions the only closure mechanism may be the zipper.

8. The vest may include a groin strap that passes from the front to the rear between the user's legs. This strap could also be equipped with thermal transfer bags.

9. The fabrics used for the vest and for the thermal transfer bags may include antimicrobial agents that inhibit the formation of odor-producing substances.

Although the preceding descriptions present considerable detail they should be properly viewed as illustrating preferred embodiments of the present invention rather than limiting the scope of the invention. Many more embodiments following the same principles will occur to those skilled in the art. Accordingly, the scope of the invention should be fixed by the following claims rather than by the examples given.

Having described my invention, I claim:

1. A thermal transfer vest, having an innermost surface, configured to be worn by a user, comprising:
   (a) a back panel;
   (b) a left yoke panel connected to said back panel;
   (c) a right yoke panel connected to said back panel;
   (d) a left front panel connected to said left yoke panel;
   (e) a right front panel connected to said right yoke panel;
   (f) said back panel, said left front panel, and said right front panel each having an interior surface, wherein said interior surface is said innermost surface of said thermal transfer vest;
   (g) a left arm relief in said back panel, said left yoke panel, and said left front panel;
   (h) a left lateral gap extending down from said left arm relief to a lower extreme of said vest;
   (i) a right arm relief in said back panel, said right yoke panel, and said right front panel;
   (j) a right lateral gap extending down from said right arm relief to said lower extreme of said vest;
   (k) a left front lateral extension on said left front panel running along said left lateral gap;
   (l) a left rear lateral extension on said rear panel running along said left lateral gap, said left front lateral extension and said left rear lateral extension configured to overlap in order to adjust a circumference of said vest;
   (m) a right front lateral extension on said right front panel running along said right lateral gap;
   (n) a right rear lateral extension on said rear panel running along said right lateral gap, said right front lateral extension and said right rear lateral extension configured to overlap in order to adjust said circumference of said vest;
   (o) an upper elastic strap running circumferentially around said vest, said upper elastic strap having a left free end, a central portion attached to said back panel, and a right free end;
   (p) a lower elastic strap running circumferentially around said vest, said lower elastic strap having a left free end, a central portion attached to said back panel and a right free end;
   (q) a first thermal transfer pack having a first hook panel, said first thermal transfer pack including a heat transfer medium that expands when transitioning to a solid but malleable state wherein said first thermal transfer pack expands when said heat transfer medium transitions to a solid and contracts when said heat transfer medium transitions back to a liquid;
   (r) a second thermal transfer pack having a second hook panel, said second thermal transfer pack including said heat transfer medium that expands when transitioning to the solid but malleable state wherein said second thermal transfer pack expands when said heat transfer medium transitions to a solid and contracts when said heat transfer medium transitions back to a liquid;
   (s) a third thermal transfer pack having a third hook panel, said third thermal transfer pack including said heat transfer medium that expands when transitioning to the solid but malleable state wherein said third thermal transfer pack expands when said heat transfer medium transitions to a solid and contracts when said heat transfer medium transitions back to a liquid;
   (t) a first area of said interior surface of said left front panel being covered in hook-compatible material, said first area being a majority of said interior surface of said left front panel and said first area being larger than said first thermal transfer pack;
   (u) said first thermal transfer pack being connected to said first area by said first hook panel such that said first thermal transfer pack is directly adhered to said interior surface of said left front panel;
   (v) a second area of said interior surface of said right front panel being covered in hook-compatible material, said second area being a majority of said interior surface of said right front panel and said second area being larger than said second thermal transfer pack;
   (w) said second thermal transfer pack being connected to said second area by said second hook panel such that said second thermal transfer pack is directly adhered to said interior surface of said right front panel;
   (x) a third area of said interior surface of said back panel being covered in hook-compatible material, said third area being a majority of said interior surface of said back panel and said third area being larger than said third thermal transfer pack;

(y) said third thermal transfer pack being connected to said third area by said third hook panel such that said third thermal transfer pack is directly adhered to said interior surface of said back panel;

(z) a vertical break between said left front panel and said right front panel, with said vertical break being selectively closable by a zipper, said vest being configured so that said user can install said first, second, and third thermal transfer packs, don said vest and close said zipper, thereafter leaving said user's hands free;

(aa) said left front panel including a left upper loop panel and a left lower loop panel;

(bb) said right front panel including a right upper loop panel and a right lower loop panel;

(cc) said upper elastic strap being configured to be stretched around said left front panel, said back panel, and said right front panel and thereafter have said left free end of said upper elastic strap be secured to said left upper loop panel and said right free end of said upper elastic strap be secured to said right upper loop panel while said zipper remains closed;

(dd) said lower elastic strap being configured to he stretched around said left front panel, said back panel, and said right front panel and thereafter have said left free end of said lower elastic strap be secured to said left lower loop panel and said right free end of said lower elastic strap be secured to said right lower loop panel while said zipper remains closed; and (ee) wherein said upper and lower elastic straps are configured to selectively and iteratively compress said first, second and third thermal packs against said user while said vertical break is closed by said zipper.

2. The thermal transfer vest as recited in claim 1, wherein said first thermal transfer pack includes a cutaway conforming to said left arm relief.

3. The thermal transfer vest as recited in claim 1, wherein said back panel, said left yoke panel, said right yoke panel, said left front panel, and said right front panel are all made as one integral piece.

4. The thermal transfer vest as recited in claim 1, further comprising:
(a) a shawl collar extending upward from said left yoke and said right yoke; and
(b) a cranial thermal pack attached to an interior surface of said shawl collar.

5. The thermal transfer vest as recited in claim 4, further comprising:
(a) a neck covering collar; and
(b) a carotid thermal pack attached to an interior surface of said posterior neck covering collar.

6. The thermal transfer vest as recited in claim 1, wherein said vest includes indicators indicating a preferred location for said thermal transfer packs.

7. The thermal transfer vest as recited in claim 6, wherein said vest includes a label indicating a preferred location for a particular thermal transfer pack.

8. A thermal transfer vest having an innermost surface configured to be worn by a user, comprising:
(a) a back panel configured to rest against a back of said user;
(b) a left front panel configured to rest against a left side of said user's torso;
(c) a right front panel configured to rest against a right side of said user's torso;

(d) said back panel, said left front panel, and said tight front panel each having an interior surface, wherein said interior surface is said innermost surface of said thermal transfer vest;

(e) a left arm relief in said back panel and said left front panel;

(f) a left lateral gap extending down from said left arm relief to a lower extreme of said vest, said left lateral gap being bounded by a first pair of edges configured to overlap in order to adjust a circumference of said vest;

(g) a right arm relief in said back panel and said right front panel;

(h) a right lateral gap extending down from said right arm relief to said lower extreme of said vest, said right lateral gap being bounded by a second set of edges configured to overlap in order to adjust said circumference of said vest;

(i) an upper elastic strap running circumferentially around said vest, said upper elastic strap having a left free end, a central portion attached to said back panel, and a right free end;

(j) a lower elastic strap running circumferentially around said vest, said lower elastic strap having a left free end, a central portion attached to said back panel, and a right free end;

(k) a first thermal transfer pack having a first hook panel, said first thermal transfer pack including a heat transfer medium that expands when transitioning to a solid but malleable state wherein said first thermal transfer pack expands when said heat transfer medium transitions to a solid and contracts when said heat transfer medium transitions back to a liquid;

(l) a second thermal transfer pack having a second hook panel, said second thermal transfer pack including the heat transfer medium that expands when transitioning to the solid but malleable state wherein said second thermal transfer pack expands when said heat transfer medium transitions to a solid and contracts when said heat transfer medium transitions back to a liquid;

(m) a first area of said interior surface of said left front panel being covered in hook-compatible material, said first area being a majority of said interior surface of said left front panel and said first area being larger than said first thermal transfer pack;

(n) said first thermal transfer pack being connected to said first area by said first hook panel such that said first thermal transfer pack is directly adhered to said interior surface of said left front panel;

(o) a second area of said interior surface of said right front panel being covered in hook-compatible material, said second area being a majority of said interior surface of said right front panel and said second area being larger than said second thermal transfer pack;

(p) said second thermal transfer pack being connected to said second area by said second hook panel such that said second thermal transfer pack is directly adhered to said interior surface of said right front panel;

(q) a vertical break between said left front panel and said right front panel, with said vertical break being selectively closable by a zipper, said vest being configured so that said user can install said first and second thermal transfer packs, don said vest and close said zipper, thereafter leaving said user's hands free;

(r) said left front panel including a left upper loop panel and a left lower loop panel;

(s) said right front panel including a right upper loop panel and a right lower loop panel;

t) said upper elastic strap being configured to be stretched around said left front panel, said back panel, and said right front panel and thereafter have said left free end of said upper elastic strap be secured to said left upper loop panel and said right free end of said upper elastic strap be secured to said right upper loop panel while said zipper remains closed;

(u) said lower elastic strap being configured to be stretched around said left front panel, said back panel, and said right front panel and thereafter have said left free end of said lower elastic strap be secured to said left lower loop panel and said right free end of said lower elastic strap be secured to said right lower loop panel while said zipper remains closed; and (v) wherein said upper and lower elastic straps are configured to selectively compress said first and second thermal packs against said user while said vertical break is closed by said zipper.

9. The thermal transfer vest as recited in claim 8, wherein said back panel includes an evaporative layer configured to be wetted and transfer heat via evaporation, wherein said evaporative layer is the outermost layer.

10. The thermal transfer vest as recited in claim 9 wherein said left front panel and said right front panel also include an evaporative layer configured to be wetted and transfer heat via evaporation.

11. The thermal transfer vest as recited in claim 8, wherein said back panel, said left front panel, and said right front panel are all made as one integral piece.

12. The thermal transfer vest as recited in claim 8, further comprising:
(a) a shawl collar extending upward from said left yoke and said right yoke; and
(b) a cranial thermal pack attached to an interior surface of said shawl collar.

13. The thermal transfer vest as recited in claim 12, further comprising:
(a) a neck covering collar; and
(b) a carotid thermal pack attached to an interior surface of said posterior neck covering collar.

14. The thermal transfer vest as recited in claim 8, wherein said vest includes an indicator indicating a preferred location for said first thermal transfer pack.

15. The thermal transfer vest as recited in claim 14, wherein said vest includes a label indicating a preferred location for said first thermal transfer pack.

* * * * *